United States Patent [19]  [11]  4,331,673
Crossley  [45]  May 25, 1982

[54] PYRIDINIUM SALTS

[75] Inventor: Roger Crossley, Reading, England

[73] Assignee: John Wyeth & Brother Limited, Maidenhead, England

[21] Appl. No.: 254,801

[22] Filed: Apr. 16, 1981

[30] Foreign Application Priority Data

Apr. 30, 1980 [GB] United Kingdom ................. 8014281

[51] Int. Cl.$^3$ .................... C07D 213/62; A61K 31/44
[52] U.S. Cl. .................................... 424/263; 546/281; 546/280
[58] Field of Search .......................... 546/281; 424/263

[56] References Cited

U.S. PATENT DOCUMENTS 4,105,776 8/1978 Ondetti et al. ...................... 424/274
4,221,912 9/1980 Ondetti et al. ...................... 546/263
4,299,769 11/1981 McEvoy et al. ............... 260/326.35

FOREIGN PATENT DOCUMENTS 1978 5/1979 European Pat. Off. ............ 548/201

OTHER PUBLICATIONS

Yamada et al., Journal of Organic Chemistry, vol. 42, No. 12, pp. 2180–2182, (1977).

Primary Examiner—Alan L. Rotman
Attorney, Agent, or Firm—Richard K. Jackson

[57] ABSTRACT

The invention concerns compounds of formula

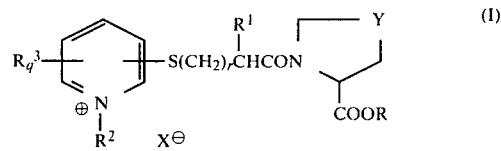

wherein the sulphur is bonded to the pyridinium ring at position 2 or 4, Y is —S— or —CH$_2$—, R represents hydrogen, or a lower alkyl group, or other carboxylic protecting group; R$^1$ represents hydrogen or lower alkyl; R$^2$ represents lower alkyl, aryl of 6 to 10 carbon atoms or aralkyl of 7 to 11 carbon atoms; R$^3$ represents hydrogen or a substituent selected from lower alkyl, halogen and lower alkoxy; q and r are each 1 or 2; and X$^\ominus$ represents a halide ion or an organosulphonate ion, which are antihypertensive agents and are useful as intermediates to captopril and analogous compounds.

5 Claims, No Drawings

PYRIDINIUM SALTS

This invention relates to novel proline derivatives possessing pharmaceutical activity, some of which are useful as chemical intermediates in the preparation of pharmaceutically active proline derivatives.

U.S. Pat. No. 4,105,776 published Aug. 8, 1978 discloses proline derivatives which are stated to inhibit the conversion of the decapeptide antiotensin I to angiotensin II and are therefore useful in reducing or relieving angiotensin related hypertension. The proline derivatives are disclosed as having general formula (A)

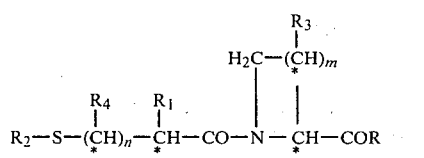

wherein R is hydroxy, $NH_2$ or lower alkoxy; $R_1$ and $R_4$ each is hydrogen, lower alkyl, phenyl or phenyl-lower alkyl; $R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

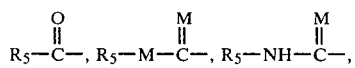

$R_6$—S— or $R_7$; $R_3$ is hydrogen, hydroxy or lower alkyl; $R_5$ is lower alkyl, phenyl or phenyl-lower alkyl; $R_6$ is lower alkyl, phenyl, substituted phenyl, (wherein the phenyl substituent is halo, lower alkyl or lower alkoxy), hydroxy-lower alkyl or amino(carboxy)lower alkyl;

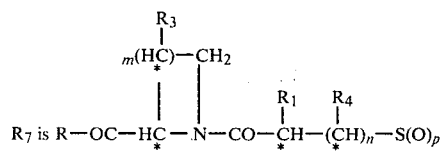

M is O or S; m is 1 to 3; n and p each is 0 to 2 and processes for preparing them.

The asterisks indicate asymmetric carbon atoms.

The preferred isomeric form is stated to be the L-isomer with respect to the carbon of the amino acid, and the D-isomer with respect to the carbon bearing $R_1$. For the purposes of the present application such a preferred arrangement of asymmetric centres is termed 'D, L configuration'.

A compound falling within the above mentioned formula and described therein, namely 1-(3-mercapto-2-D-methylpropanoyl)-L-proline having the generic name captopril, has been extensively investigated and found to be a potent antihypertensive agent (see for example, D. W. Cushman et al., *Biochemistry*, Vol. 16, 5484 (1977); D. W. Cushman et al., *Proc. in Cardiovascular Diseases*, Vol. XXI, No. 3, 183 (1978); *Chemistry and Engineering*, April 4, 21 (1977); and H. Gavras et al., *New Eng. J. Med.*, Vol. 298, No. 18, 991 (1978)). This compound has the preferred D, L configuration.

U.S. Pat. No. 4,105,776 also describes a route for the preparation of captopril and related compounds using as intermediates compounds of formula (B)

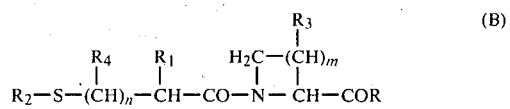

wherein R, $R_1$, $R_3$, $R_4$, m and n are as defined above and $R_2$ is a group derived from a thioacid of formula $R_2$—SH.

In addition European Patent Publication No. 1978 discloses 3-mercapto-2-methylpropanoyl-4-thiazolidine carboxylic acid which has potent antihypertensive activity.

We have now found a class of pyridinium salts which possess pharmaceutical activity and can be used in pharmaceutical compositions. Furthermore, some of these salts can be used as intermediates in a particularly convenient route to captopril and analogous mercapto compounds. These intermediates possess the characteristics of (i) ready convertion to the final products, (ii) easy purification by crystallisation and (iii) facile separation of stereoisomeric forms where mixtures are initially produced.

Accordingly this invention provides compounds of formula:

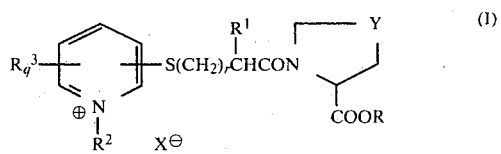

wherein the sulphur is bonded to the pyrinidium ring at position 2 or 4, Y is —S— or —$CH_2$—, R represents hydrogen, or an alkyl group, or other carboxylic protecting group; $R^1$ represents hydrogen or lower alkyl; $R^2$ represents alkyl, aryl or aralkyl; $R^3$ represents hydrogen or a substituent, e.g. alkyl, halogen or alkoxy; q and r are each 1 or 2; and $X^\ominus$ represents a halide ion or an organosulphonate ion, e.g. aryl- or aralkyl- or alkyl-sulphonate ion such as p-toluenesulphonate- or methanesulphonate.

By the term "lower alkyl" are used herein is meant a branched or straight chain alkyl group having one to seven carbon atoms, such as methyl, ethyl, n-propyl, isopropyl or n-butyl. Lower alkyl groups having up to 4 carbon atoms are preferred and methyl is most preferred.

The term 'halogen' means chlorine, fluorine, bromine or iodine.

Examples of alkyl groups for $R^2$ and $R^3$ are lower alkyl groups as described above. Preferably r is 1 and $R^3$ is hydrogen.

The compounds of formula I possess angiotensin converting enzyme (ACE) inhibitory activity and hence are useful as anti-hypertensive agents. The procedure used for detecting ACE inhibitory activity was as follows:

Normotensive female rats (300–350 g) were anaesthetised with sodium pentobarbitone (50 mg/kg ip). Blood pressure was monitored from the femoral artery and drugs were administered via a cannula in the femoral vein. The trachea was cannulated to facilitate spontaneous respiration.

Dose response relationships were defined for angiotensin I (AI) and angiotensin II (AII) and constant submaximal doses were determined to give reproducible pressor response of about 40 mmHg. In general these doses were in the 0.1–0.2 μg range.

When constant submaximal responses had been obtained to both AI and AII, the test compound was administered cumulatively. Ten minutes after each administration of the compound the doses of AI and AII were repeated and the dosing cycle continued.

In the above mentioned test procedure a representative compound of formula I, namely N-[2-methyl-3-([1-methylpyridinium-2-yl]thio)propionyl]-L-proline bromide, gave the following results:

| Compound | Dose (mg/kg) | Pressor response to Angiotensin I % Predose | Angiotensin II % Predose |
|---|---|---|---|
| 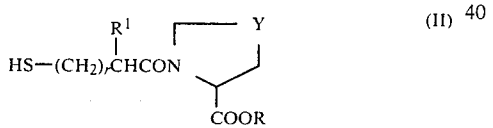 Br⊖ (A) | 0.01 | 100 | 102 |
| | 0.1 | 104 | 80 |
| | 1 | 85 | 77 |
| | 10 | 33 | 98 |

These results show that the compound (A) possessed substantial ACE inhibitory activity and accordingly is useful as an antihypertensive agent.

Furthermore as mentioned above the compounds of formula I are useful as intermediates to captopril and analogous compounds and provide a convenient means for introducing the mercapto function into the final products. Accordingly this invention also provides a process for preparing a compound of formula $$\text{HS}-(CH_2)_r\overset{R^1}{\underset{|}{C}}HCON\underset{COOR}{\overbrace{\phantom{XXXX}}^{Y}} \quad (II)$$

wherein Y,R,R¹ and r are as defined above which comprises reacting a compound of formula I as hereinbefore defined with an alkali metal hydroxide, e.g. sodium hydroxide, potassium hydroxide, and if desired converting a compound of formula II wherein R is an ester or other carboxy protecting group to a compound of formula II wherein R is hydrogen.

This reaction may be carried out in a suitable solvent such as water or a lower alkanol, e.g. methanol or ethanol or a mixture thereof. The reaction proceeds at room temperature.

In a preferred embodiment of the aforementioned reaction process the compound of formula I is one wherein R¹ is methyl and r is 1, the configuration of the propionyl α-carbon is D and the proline α-carbon is L. The product of the reaction using such a starting material is captopril itself when R is hydrogen.

Because the compounds of formula I are salts they are particularly useful as intermediates when it is desired to prepare compounds of formula II having specific stereochemistry. The separation of diastereoisomers from mixtures is generally more easily achieved when diastereoisomers are salts. Thus the compounds of formula I therefore provide a convenient stage in the synthesis of captopril type compounds at which to isolate the preferred stereochemical isomer having the D,L configuration of asymmetric centres.

This invention also provides a process for preparing a compound of formula I which comprises reacting (A) a pyridothione of formula III or IV

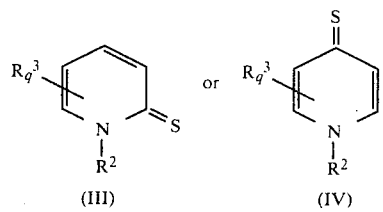

wherein R², R³, q and X are as hereinbefore defined, with a compound of formula

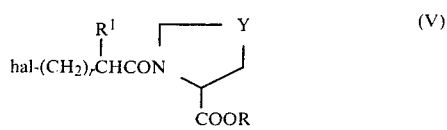

wherein hal is halogen; Y,R, R¹ and r are as hereinbefore defined, or (B) a compound of formula II

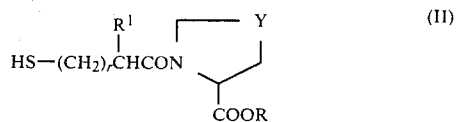

wherein Y, r, R and R¹ are as hereinbefore defined with a compound of formula

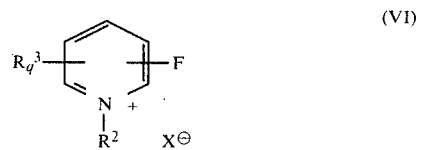

wherein X⊖, R², R³ and q are as hereinbefore defined, and the fluorine is in position 2 or 4, or (C) a compound of formula VII

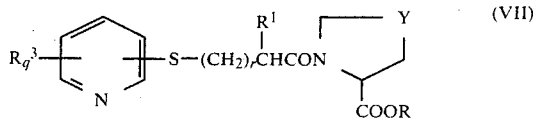

wherein the sulphur is bonded to position 2 or 4 of the pyridine ring, and r, q, R, R¹, Y and R³ are as hereinbefore defined, with an alkylating, arylating or aralkylating agent containing the groups R² and X, e.g. a lower alkyl- or aralkyl- halide or a lower alkyl-, aryl- or aralkyl-sulphonic acid lower alkyl or aralkyl ester.

A compound I in which X⊖ is one particular anion may be converted to another in which X⊖ is a different anion by anion exchange, e.g. chloride may be exchanged for iodide by reaction of a chloride of formula I with sodium iodide in ethanol or other suitable solvent.

After any of the aforementioned reactions individual diastereoisomers of formula I may be isolated by conventional means, e.g. fractional crystallisation, high performance liquid chromatography.

The invention includes a method of treating hypertension in a mammal which method comprises administering to said mammal an effective amount of an antihypertensive agent of formula I as defined above. The amount used will depend on the needs of the mammal being treated and the activity of the compound used but may vary from 1 to 100 mg/kg.

The invention also provides a pharmaceutical composition comprising a compound of general formula (I) or a pharmaceutically acceptable salt thereof in association with a pharmaceutically acceptable carrier. Any suitable carrier known in the art can be used to prepare the pharmaceutical composition. In such a composition, the carrier is generally a solid or liquid, or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg. or less to 750 mg. or more, according to the particular need and the activity of the active ingredient. The invention also includes the compounds in the absence of the carrier where the compounds are in unit dosage form.

The following Examples illustrate the invention:

EXAMPLE 1

N-[2-Methyl-3-([1-methylpyridinium-2-yl]thio)propionyl]-L-proline bromide (a) A solution of N-(3-bromo-2-methylpropionyl)-L-proline (1.0 g) and 1-methyl-2-pyridothione (0.5 g) in acetonitrile (25 ml) was heated at reflux for 5 hours. The solvent was removed by evaporation and the residue was triturated with ether and then with acetone to give a solid. This solid was removed by filtration and dried to give the title compound, hemihydrate (0.2 g), m.p. 170°–5° C.

Analysis Found: C, 45.1; H, 5.3; N, 6.7 $C_{15}H_{21}BrN_2O_3S.\frac{1}{2}H_2O$ requires C, 45.2; H, 5.6; N, 7.0%.

(b) A solution of the product of step (a) above in a mixture of 10% methanol and 90% acetonitrile was fractionally crystallised to give N-[2-D-methyl-3-[1-methylpyridinium-2-yl]thio)propionyl]-L-proline bromide.

EXAMPLE 2

1-(3-Mercapto-2-D-methylpropionyl)-L-proline

N-[2-D-Methyl-3([1-methylpyridinium-2-yl]thio)propionyl]-L-proline bromide (3.98 g) prepared according to Example 1(b) was dissolved in methanol (40 ml) and the solution was treated with a solution of sodium hydroxide (0.4 g) in methanol (40 ml). The solvent was removed by evaporation and the residue was dissolved in chloroform and filtered to remove sodium bromide. The residue was evaporated and triturated with ethyl acetate to give the title compound.

EXAMPLE 3

N-[2-Methyl-3-([1-benzylpyridinium-2-yl]thio)propionyl]-L-proline bromide

Using a procedure analogous to Example 1, N-(3-bromo-2-methylpropionyl)-L-proline and 1-benzyl-2-pyridothione are reacted to give the title compound.

EXAMPLE 4

N-[2-methyl-3-([1-phenylpyridinium-2-yl]thio)propionyl]-L-proline bromide

Using a procedure analogous to Example 1 N-(3-bromo-2-methylpropionyl)-L-proline and 1-phenyl-2-pyridothione are reacted to give the title compound.

EXAMPLE 5

N-[2-Methyl-3-([1,6-dimethylpyridinium-2-yl]thio)propionyl]-L-proline bromide

Using a procedure analogous to Example 1 N-(3-bromo-2-methylpropionyl)-L-proline and 1,6-dimethylpyridothione are reacted to give the title compound.

EXAMPLE 6

3-[2-Methyl-3-([1-methylpyridinium-2-yl]thio)propionyl]-4-thiazolidinecarboxylic acid, bromide Using a procedure analogous to Example 1 3-(3-bromo-2-methylpropionyl)-4-thiazolidinecarboxylic acid is reacted with 1-methyl-2-pyridothione to give the title compound.

EXAMPLE 7

N-[2-Methyl-3-([1-methylpyridinium-2-yl]thio)propionyl]-L-proline, tosylate

Using a procedure analogous to Example 1 N-(3-tosyloxy-2-methylpropionyl)-L-proline and 1-methyl-2-pyridothione are reacted to give the title compound.

I claim:

1. A compound of the formula

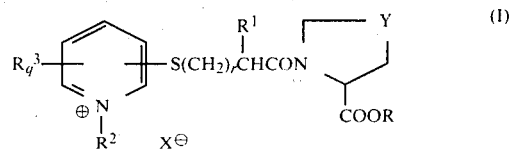

wherein the sulphur is bonded to the pyridinium ring at position 2 or 4, Y is —$CH_2$—, R represents hydrogen, or lower alkyl group, or other carboxylic protecting group; $R^1$ represents hydrogen or lower alkyl; $R^2$ represents lower alkyl, aryl of 6 to 10 carbon atoms or aralkyl or 7 to 11 carbon atoms; $R^3$ represents hydrogen or a substituent selected from lower alkyl, halogen and lower alkoxy; q and r are each 1 or 2; and $X^\ominus$ represents a halide ion or an organosulphonate ion.

2. A compound of formula I according to claim 1 wherein R is hydrogen, $R^2$ is lower alkyl and $R^3$ is hydrogen.

3. A compound of formula I according to claim 1 wherein the sulphur is bonded to the pyridinium ring at position 2.

4. A compound of formula I which is N-[2-methyl-3-([1-methylpyridinium-2-yl]thio)propionyl]-L-proline bromide.

5. A pharmaceutical composition comprising an antihypertensive effective amount of a compound of formula I as claimed in claim 1 and a pharmaceutically acceptable carrier.

* * * * *